United States Patent
Shchepinov et al.

(10) Patent No.: US 6,809,220 B2
(45) Date of Patent: Oct. 26, 2004

(54) TRITYL-TYPE COMPOUNDS AND THEIR USE

(75) Inventors: Mikhail Sergeevich Shchepinov, Oxford (GB); Edwin Mellor Southern, Oxford (GB)

(73) Assignee: Isis Innovations, Ltd. (GB)

( * ) Notice: Subject to any disclaimer, the term of this patent is extended or adjusted under 35 U.S.C. 154(b) by 0 days.

(21) Appl. No.: 10/240,383

(22) PCT Filed: Mar. 28, 2001

(86) PCT No.: PCT/GB01/01380

§ 371 (c)(1),
(2), (4) Date: May 19, 2003

(87) PCT Pub. No.: WO01/72926

PCT Pub. Date: Oct. 4, 2001

(65) Prior Publication Data

US 2003/0175742 A1 Sep. 18, 2003

(30) Foreign Application Priority Data

Mar. 28, 2001 (GB) .............................. 0007530

(51) Int. Cl.[7] .............................. C07C 233/65
(52) U.S. Cl. ................. 564/172; 530/300; 530/350; 536/22.1
(58) Field of Search .................. 564/172; 530/300, 530/350; 536/22.1; 514/617

(56) References Cited

U.S. PATENT DOCUMENTS

| | | |
|---|---|---|
| 3,257,413 A | 6/1966 | Short |
| 5,344,985 A | 9/1994 | Tanaka et al. |
| 5,382,692 A | 1/1995 | Shimada et al. |

OTHER PUBLICATIONS

Hansen et al, J. Org. Chem., vol. 63, pp. 1827–1835, 1998.*

Fourrey, J.L., et al., "1,1–Bis–(4–Methoxyphenyl–1'–Pyrenyl Methyl (bmpm): A New Fluorescent 5'Protecting Group for the Purification of Unmodified and Modified Oligonucleotides", *Tetrahedron Lett.* (1987), pp. 5157–5160, vol. 28, No. 43; Pergamon Journals Ltd., Great Britain.

Wittig, G., et al., "Bildung und Nachweis von 9.10–Dehydrophenanthren", *Chemische Berichte* (1962), pp. 1692–1702, XP–002155250.

Leikauf, E., et al., "A Combinatorial Protecting Group Strategy for Oligonucleotide Synthesis", *Tetrahedron* (1996), pp. 6913–6930, vol. 52, No. 20; Elsevier Science Limited; Great Britain.

Bersheid, R. and Vögtle, F. "Concave Dyestuffs: A Triply Bridged Triphenylmethyl Dication", *Synthesis* (1992), pp. 6913–6930, vol. 52, No. 20; XP–002155252.

Biernat, J., et al., "Purification Orientated Synthesis of Oligodeoxynucleotides in Solution", *Tetrahedron Lett.* (1983), pp. 751–754, vol. 24, No. 8; XP–002155253; Pergamon Press Ltd., Great Britain.

Gildea, B., et al., "A Versatile Acid–Labile Linker for Modification of Synthetic Biomolecules", *Tetrahedron Lett.* (1990), pp. 7095–7098, vol. 31, No. 49; XP–000172821; Pergamon Press plc, Great Britain.

Leikauf, E., et al., "Heterobifunctional Trityl Derivatives as Linking Reagents for the Recovery of Nucleic Acids after Labeling and Immobilization", *Tetrahedron* (1995), pp. 3793–3802, vol. 51, No. 13; XP–002155254; Elsevier Science Limited; Great Britain.

* cited by examiner

*Primary Examiner*—Shailendra Kumar
(74) *Attorney, Agent, or Firm*—Saliwanchik, Lloyd & Saliwanchik

(57) ABSTRACT

The present invention pertains to trityl-type compounds comprising, bonded to the same atom, three aryl groups, of which at least one is a fluorophore and at least one has a substituent including a functional group, and wherein the compound can exist in a non-ionised state or in an ionised state conjugated with the aryl groups.

5 Claims, 5 Drawing Sheets

TRITYL-TYPE COMPOUNDS AND THEIR USE

This application is a 371 of PCT/GB01/01380, filed Mar. 28, 2001.

FIELD OF THE INVENTION

This invention relates to trityl-type compounds and to their use as fluorescent labels for solution and solid support applications.

BACKGROUND OF THE INVENTION

Triarylmethyl (trityl)-type cations are stabilised by the resonance effect of the phenyl rings, which makes their ethers acid-labile, and they are consequently a useful family of protective groups, especially in nucleoside chemistry (1). Conjugation to a positively charged (cationic) carbon atom dramatically changes the spectral properties of the fluorophore. Trityl groups generating cations of different colours have been used to protect different nucleotides in oligonucleotide synthesis (2).

A modified trityl group bearing a pyrenyl residue in place of one of the aryl groups has fluorescent properties similar to non-modified pyrene and has been used, in its non-cationic (non-charged) form, for more precise fluorescent detection (down to $10^{-10}$ M) of detritylation (3). The modified trityl compound is attached to a nucleoside by linkage to the carbon atom. Triphenylmethyl-based structures bearing a side-chain have been used to reversibly label synthetic oligonucleotides with biotin, etc (4), to purify them by immobilisation on to a solid support after synthesis (5), and to controllably activate prodrug antibody conjugates (6). These trityl-based structures combine the useful properties of a trityl group (easy cationisation, and easy control of the rate of cationisation, by introducing more or less methoxy groups) with a 'hook' which keeps them in the right place even after ionization, unlike more conventional trityl-based protective groups.

Various (non-acidic) ways of removing the triarylmethyl protective group are known. These include treatment with anion radicals (7), $ZnBr_2$ (8) and irradiation of the starting material (photochemical ionization) (9).

Derivatives of trityl groups with different masses have been used as unique mass-tags in combinatorial synthesis (10). They benefit from the high desorption rate of triphenylmethyl cation-based tags under conditions of laser desorption/ionisation time of flight (TOF) mass-spectrometry. Again, the trityl cations could be released either by acidic treatment or directly by laser irradiation. In the latter case, it can be beneficial to tune the absorbance of the tag more finely, by making it closer to the wavelength of the laser used for ionization of the sample, in a way similar to that described for porous silica used as a matrix (11).

Both single fluorophore (12) and energy transfer (13–17)-based fluorescence detection methods find wide applications in the analysis of nucleic acids.

SUMMARY OF THE INVENTION

The present invention is based, firstly, on the discovery of new multi-purpose fluorescent tags derived from polycyclic aromatic hydrocarbons (PAHs).

According to a first aspect of the invention, a trityl-type compound comprises, bonded to the same atom, three aryl groups, of which at least one is a fluorophore and at least one has a substituent including a functional group, and wherein the compound can exist in a non-ionised state or in an ionised state conjugated with the aryl groups. Such compounds can be soluble, have controllable fluorescence, and can be used, in the form of phosphoramidites, for nucleotide synthesis, or in dendrimers.

Having the functional group located on one of the aryl groups, permits the compound to undergo ionisation while at the same time being joined to another molecule or solid support. This is in contrast to the prior art where the fluorescent trityl-type compounds are bound to other molecules through the central carbon atom.

In a second aspect of the present invention, a fluorescence-resonant compound is obtainable by linking two different trityl-type compounds each comprising three aryl groups of which at least one has a substituent including a functional group, and wherein each trityl-type compound can exist in a non-ionised state or in an ionised state conjugated with the respective aryl groups, the linking being via the respective functional groups. Such compounds are useful in FRET, eximer and other energy-transfer systems where the ability to modulate different fluorescent signals by altering the reaction conditions, can be beneficial.

DESCRIPTION OF THE DRAWINGS

The accompanying drawings illustrate the invention, where.

DESCRIPTION OF THE INVENTION

Figure 1:
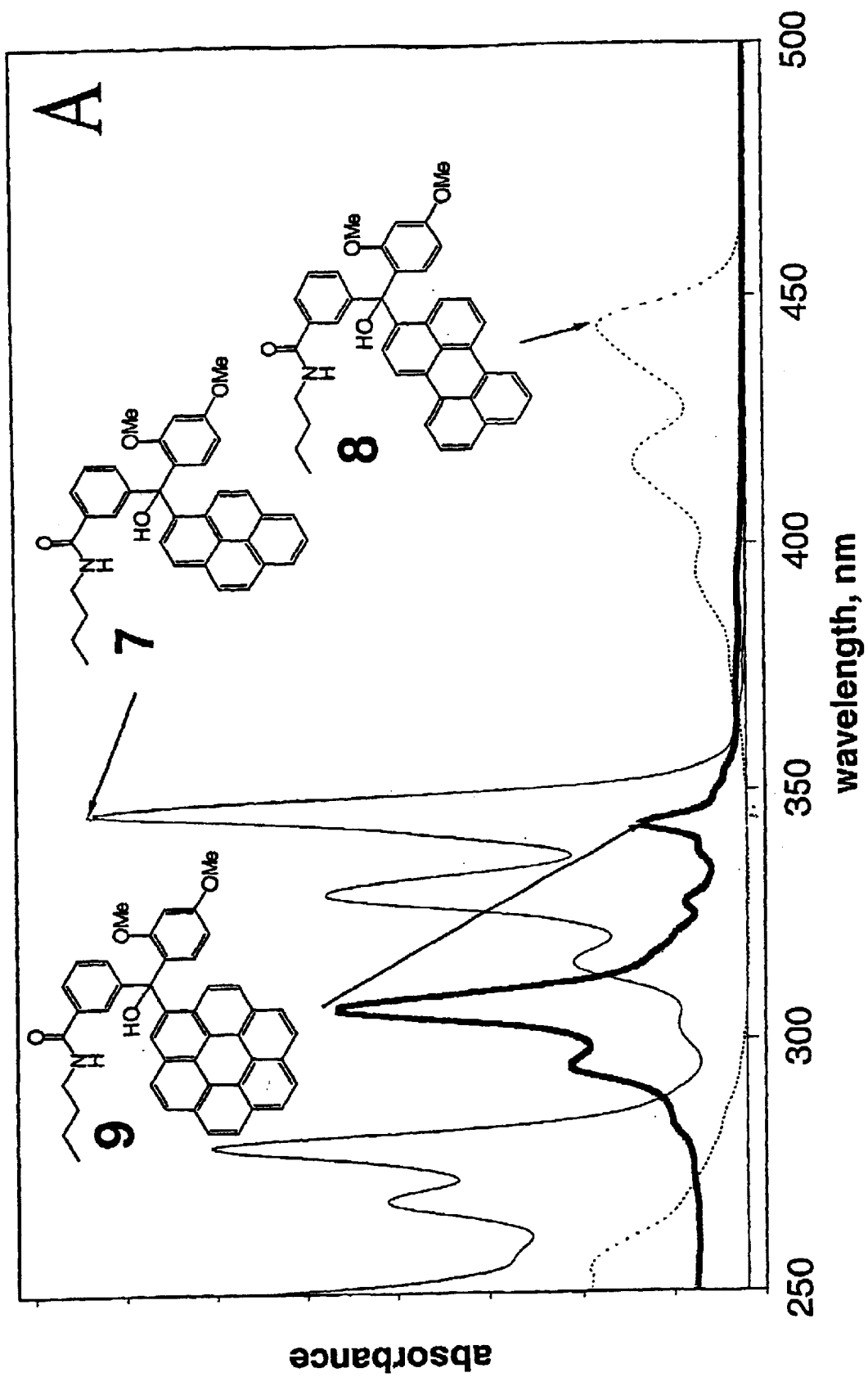
FIG. 1 illustrates the absorbance maximum for three compounds 7, 8 and 9.

The functional group that is present in compounds of the invention is intended to allow bonding (covalent bonding) to another molecule, e.g. a biomolecule or solid support. Examples of suitable functional groups are well known to those skilled in the art. For example, they may comprise a functionalised C atom, from which a C—C bond may be formed. A typical example includes —CO—NH—. The functional group may be, for example, an ethylenically unsaturated group, an acetylenically unsaturated group, or an acyl, carbonyl, carboxylic, amine, sulphide, phosphate, silane or hydroxy group. The functional group may be attached to the aryl group through a linker molecule, for example an alkanediyl, alkenediyl or alkynediyl group.

Molecules that may be attached to the trityl-type compounds through the functional group include nucleic acids, e.g. nucleosides or ribonucleosides (including polynucleotides), amino acids or peptides, solid support materials of functionalised ligands attached to solid supports. Compounds of this invention may be used either in solution or in immobilised (surface-bound) form.

The synthesis of trityl-type compounds is well known to those skilled in the art, and is illustrated in references cited herein. The fluorescent group is preferably a PAH that may be introduced as one of the aryl groups, or it may be added to a pre-formed trityl group. The term "trityl-type" is used herein to define compounds suitable for use in the invention, and is not to be understood as limited to $(Ph)_3C$ groups.

Polycyclic aromatic hydrocarbons suitable for use in the invention will be apparent to the skilled person. For example, the PAH may comprise 2, 3, 4, 5, 6 or more fused benzene rings. The polycyclic ring structures may be substituted or unsubstituted.

PAHs may have advantages over the fluorophores commonly used to label DNA, such as fluorescein: they are less prone to photobleaching and have high molar absorbance and high quantum yields; molecules are available with a range of excitation and emission maxima and large Stokes' shifts. Typical examples of PAHs with attractive fluorescent properties include pyrene, perylene, coronene and rubrene.

The introduction of a carbinol-carbocation switchable element allows one to controllably modulate the fluorescence properties by changing the pH (Scheme 2). The central atom does not necessarily have to be a carbon atom, but may be any atom capable of being in an ionised form while at the same being bound to the three aryl groups. Alternative designs may include triarylamines and triarylsulphonium salts, which both possess a central atom bearing p-orbits which conjugate the aryls together. Therefore, a general structure of the compounds is:

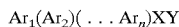

where each Ar is aryl, at least one of the aryls is a fluorophore, and at least one of the aryls has a side-chain with a reactive group/function at the end;

X is a central atom, most likely carbon or nitrogen, but which also could be sulphur, and potentially even phosphorus, boron, etc;

n is at least 3 (depending on the nature of X) and may be for example 4, 5 or 6; and Y is an optional group, which for example is present when X=C, and may be, for example, halogen, OH, OR, $NH_2$, NHR, SR, etc, where R may be an alkyl group.

The presence of a PAH in these structures induces a non-planar conformation of the compounds, whether triarylmethanols, tertiary amines, sulphonium salts, triarylphosphines, etc. This prevents stacking interactions between PAH molecules, which reduce solubility.

A modified trityl group bearing a pyrenyl residue in place of one of the phenyls has fluorescent properties similar to non-modified pyrene (3). The triarylmethyl cation derived from tritanol by an acidic treatment has completely different fluorescence properties, while remaining covalently linked to a 'probe' molecule (biomolecule, solid support, etc) if attached to it through a side-chain (4). These features are combined in compounds 4a–c shown below in Scheme 1.

Preferably, at least two of the aryl groups are differently substituted; this term is used to include the possibility that one of the differently substituted groups is unsubstituted. More preferably, the pH-threshold for the formation of trityl carbocations (such as compound 6) from corresponding tritanols at low pH can be controlled by electron-withdrawing or donating groups in the aromatic rings (1). Two methoxy groups and one carboxyl group give the model compounds 7–9 (obtained by reaction of compounds 4a–c with butylamine) which have acidic stability similar to that of a standard DMTr and MMTr groups (namely, the acidic stability of 7–9 (2% $TsOH/CH_2Cl_2$) was as follows: DMTrOH<7<9 MMTrOH<8<TrOH). The UV spectra of 7–9 were of the same shape but slightly (3–10 nm) red-shifted as compared to the starting PAHs (18). In the following chemical formulae, the OH group is attached directly to the central carbon atom. The shown attachment represents the bond that is broken on ionisation, and does not represent an intermediate alkyl group.

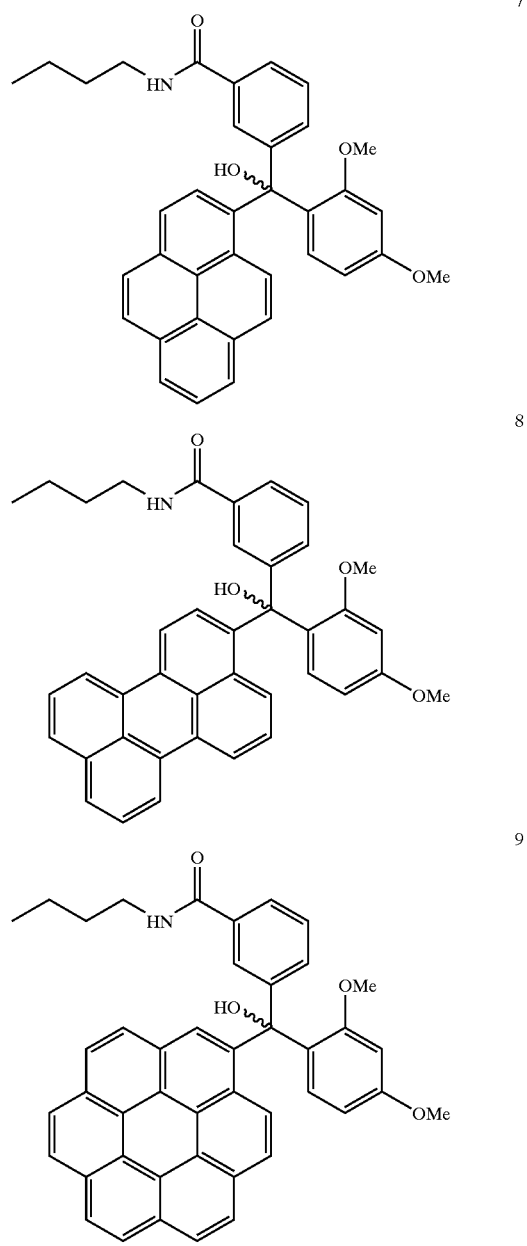

Figure 2:
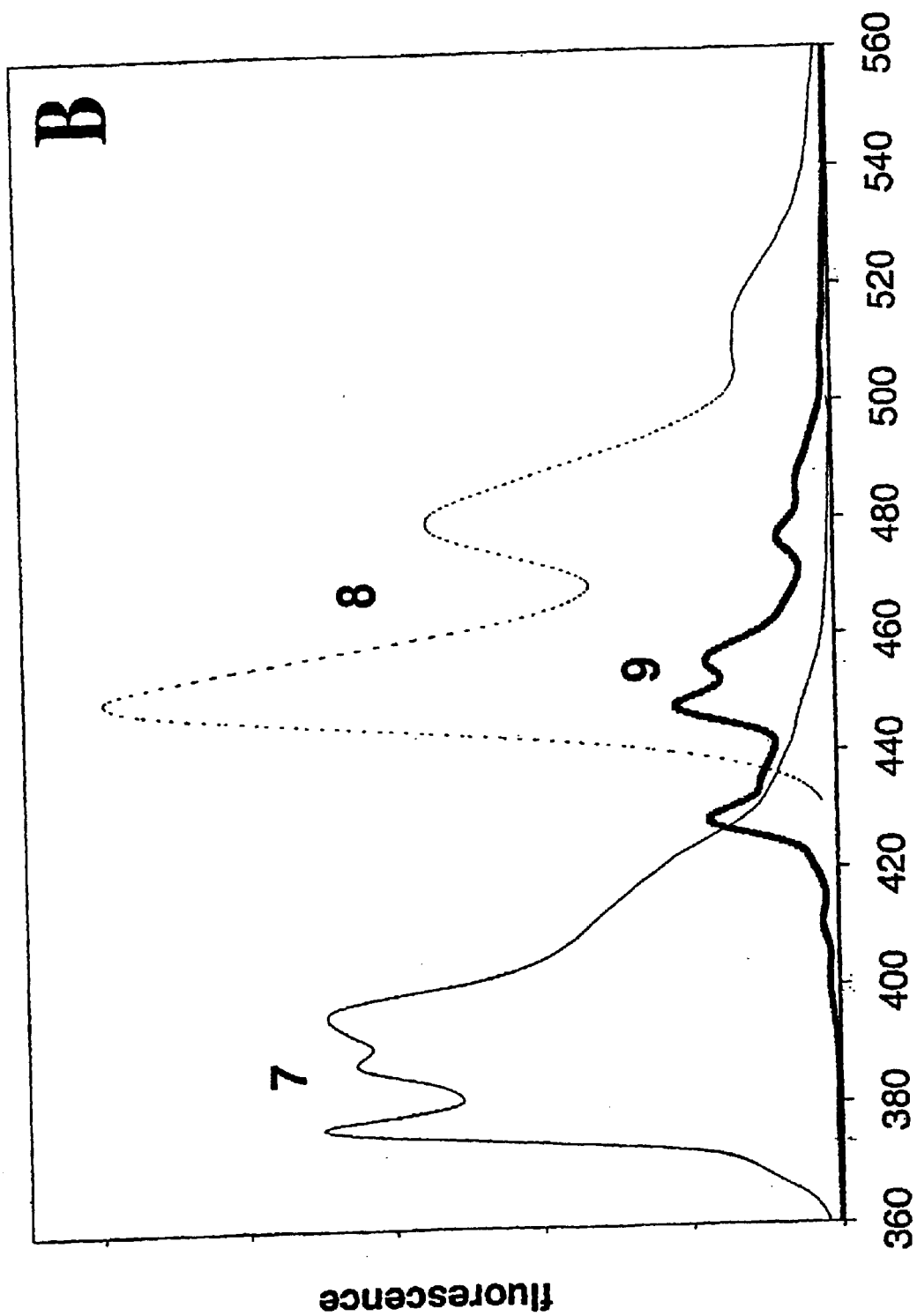
FIG. 2 illustrates the fluorescence for each of 7, 8 and 9.
Figure 3:
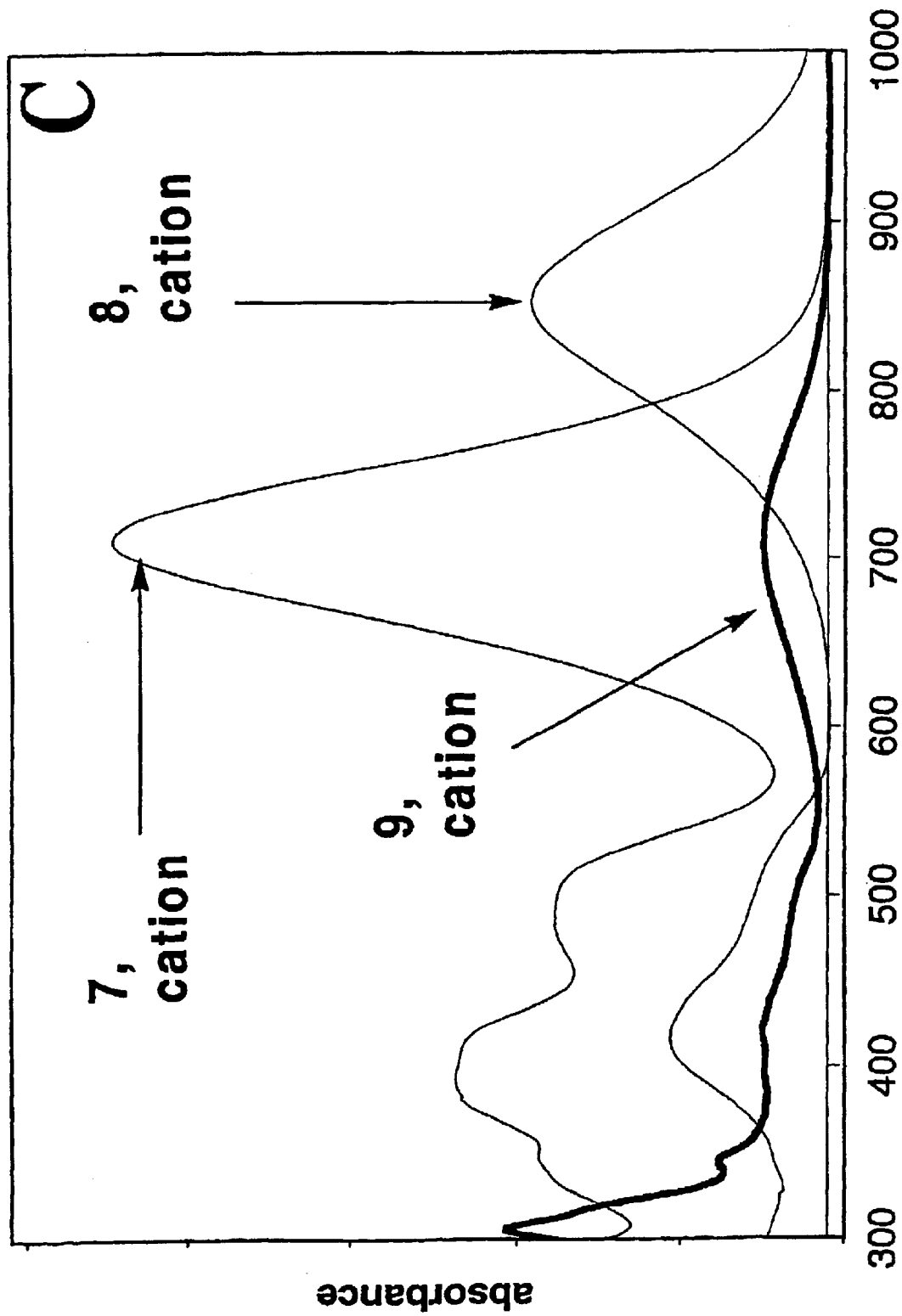
FIG. 3 illustrates the different absorbance values when 7, 8 and 9 are in the cationic form.

Multicolour detection is a useful feature of fluorescent dyes widely used in modern DNA analysis; it enables different sequences to be detected simultaneously and has been used to good effect, for example, in DNA sequencing (12) and differential gene expression analysis on DNA chips (19). The size of the palette is limited by overlap of the excitation and emission spectra; it has proved difficult to use more than four colours in FISH and two colours are normal in expression analysis. An advantage of trityl-based fluorescent tags is the potential to switch the spectra by simply changing the pH. The magnitude of the shifts is very large, and this property has previously been used to generate triarylmethyl carbocations with a variety of different colours (2). For example, moving from neutral or alkaline to acidic pH shifts the excitation maximum of the pyrene-based compound 7 from 346 nm to 711 nm (FIGS. 1–3).

Trityl carbocations do not fluoresce in the range detected for the corresponding tritanols. This property can be used to improve the discrimination of labels: firstly, by increasing the accuracy of intensity measurements; and, secondly, by increasing the potential number of colours in the palette. For example, targets may be labelled with two fluorophores having similar excitation and emission spectra, but only one of which is switchable by pH change. After hybridisation, measurements are taken at two pH values: under ambient conditions and after exposing the array to acidic vapour, which is enough to switch the emission of fluorescent trityls immediately, but reversibly. Using a single excitation source, both fluorophores emit at neutral pH but only one will emit in acid. These two measurements alone would be enough to distinguish the two patterns of hybridisation. But a third measurement, using a source which excites the second fluorophore in acid, gives more data. In this way, the number of labels that can be used together may be doubled.

In the second aspect of the invention, two trityl-type molecules are linked. Essentially, the only requirement of the linker between the two molecules is that it should be of an appropriate length. It will typically comprise at least predominantly C atoms and optionally also O and/or N atoms.

To evaluate the suitability of the novel fluorescent labels as components for analysis procedures which utilise fluorescence resonance energy transfer (FRET), a model compound 10 was synthesised.

Figure 4:
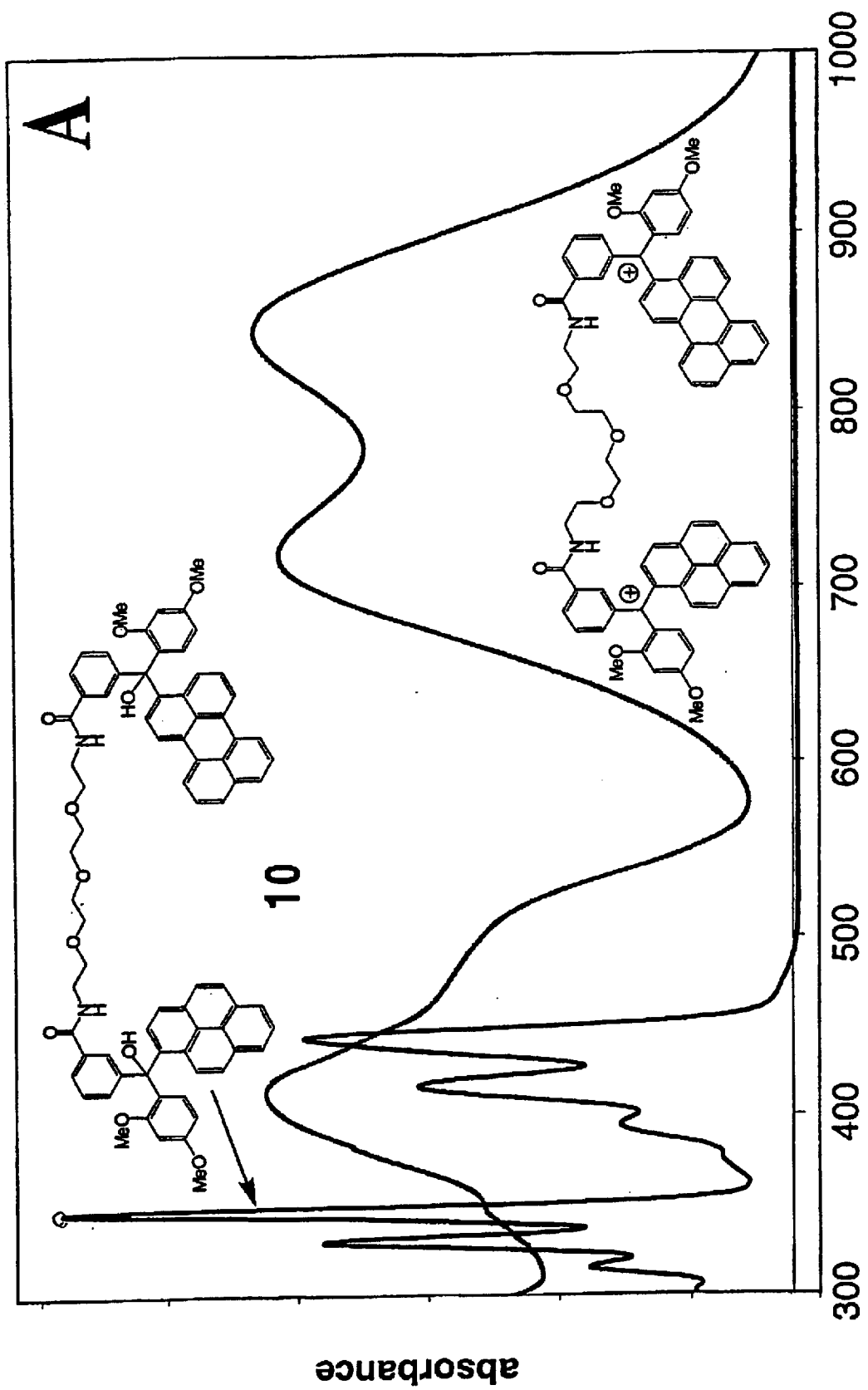
FIG. 4 illustrates the different absorbance values for the cationic and non-cationic forms of compound 10.
Figure 5:
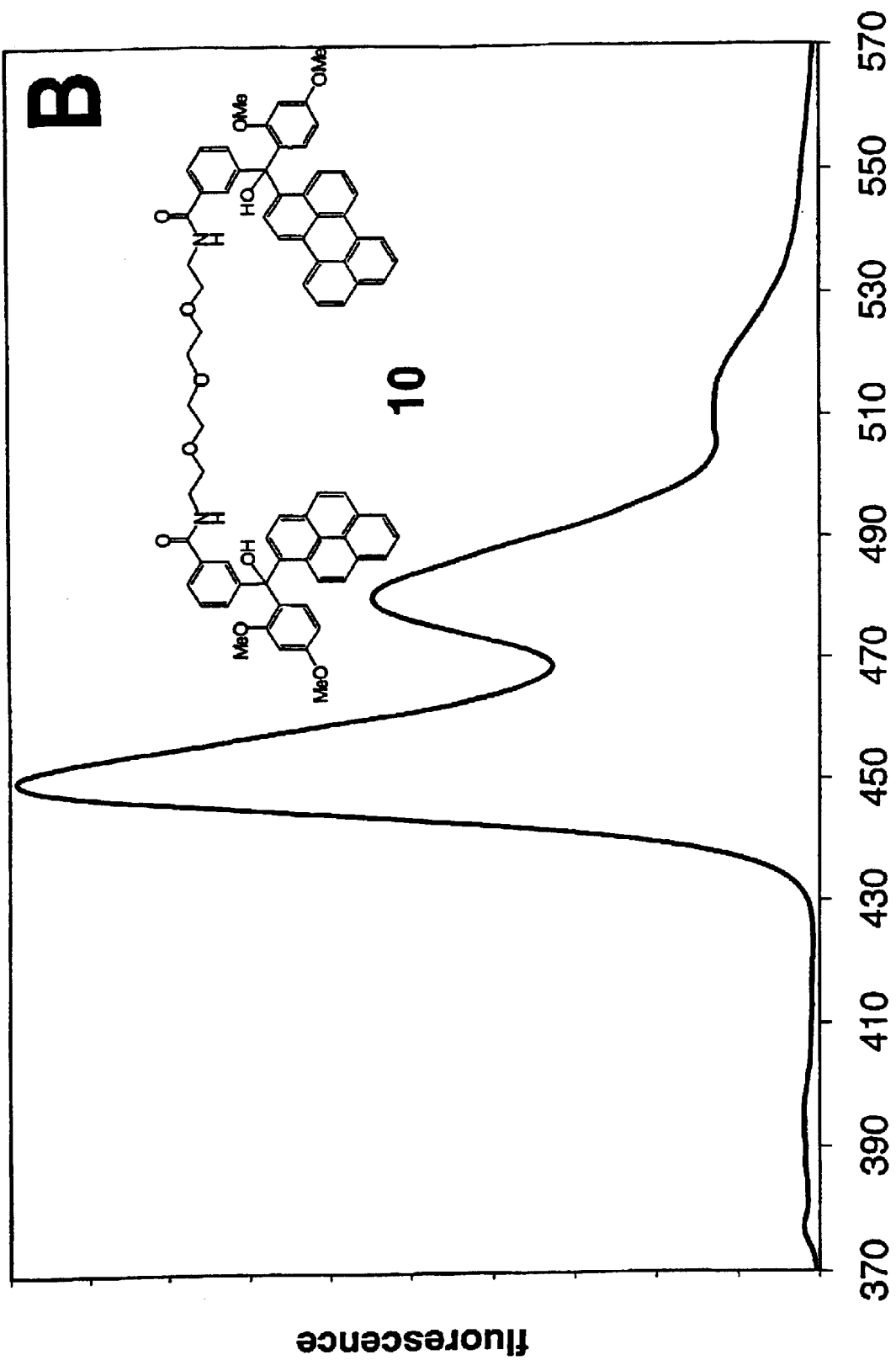
FIG. 5 illustrates the fluorescence of compound 10 in the non-cationic form.

While having absorption spectra similar to those of 7 and 8, it fluoresces only at 450 nm and 480 nm when excited at pyrene absorption maximum of 346.5 nm (FIGS. 4 and 5), with no detectable fluorescence of pyrene (377 nm, 388 nm and 396 nm), thus demonstrating a complete resonance transfer of energy with high quantum yield (when mixed in equimolar amounts, 7 and 8 retain their own fluorescence properties). The effect of this is to endow the new compound with an exceptionally high Stokes' shift. The independent control of fluorescent properties of each of the two parts of a FRET couple can give rise to additional features previously unavailable. For example, if in 10 the pyrenyl moiety (on the left) is made much easier to ionise (for example, by introducing three methoxy groups) than the perylenyl moiety on the right, then at neutral pH the system will work as a FRET couple, whereas at slightly lower pH, at which the pyrenyl part will, but the perylenyl part will yet not be in cationic form, the absorbance of pyrenyl moiety will be shifted to about 700 nm, thus preventing the FRET. Further selection of fluorophores (for instance, perylene and rubrene) may lead to the systems in which one part of the molecule can be transformed from a FRET donor to a FRET acceptor, etc. Other possibilities include more than two components in the FRET chain, each of which could be selectively activated or deactivated. The term "fluorescent-resonant" is used herein to indicate that there is at least one set of conditions under which resonance can occur.

The utility of trityl cations with different masses as unique mass-tags depends on the efficiency (rate) of their formation from corresponding triarylmethyl ethers and desorption upon laser irradiation (10). The wavelength of the laser used in most (MA)LDI-TOF instruments (340 nm) is about 70 nm red-shifted as compared to the absorbance maximum of DMTr- and MMTr- based mass-tags. A closer match in wavelength may lead to the trityl group's being a better energy receptacle for the laser radiation; this may improve the cleavage/desorption efficiency and thus also other parameters such as detection sensitivity. The absorbance maximum of 7 is 343 nm (FIG. 1) which is almost a

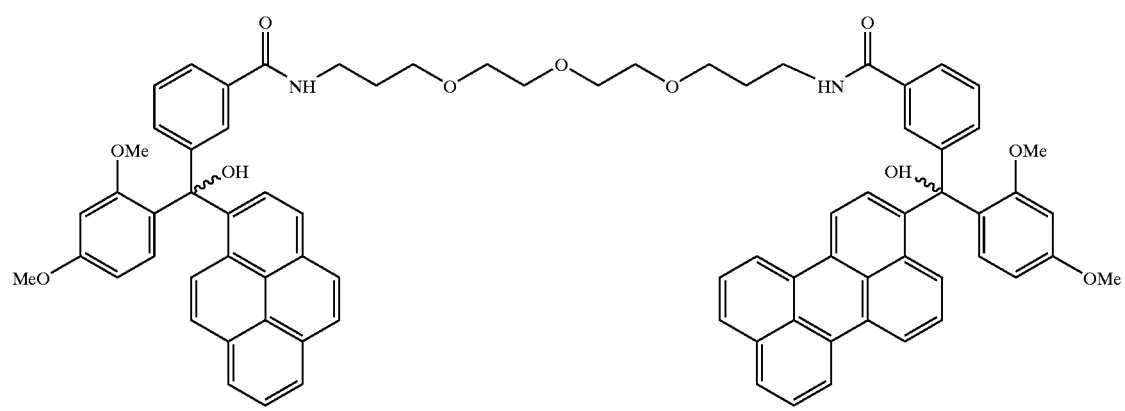

10 complete match with the laser wavelength; indeed, when used as a mass-tag, compound 7 has desorption properties comparable to those for DMTr-based mass-tags.

In a similar way, it is possible to tune the wavelengths at which the cis-trans transformation of azobenzene takes place. For a non-modified compound 14, it is from 350 nm to more than 400 nm.

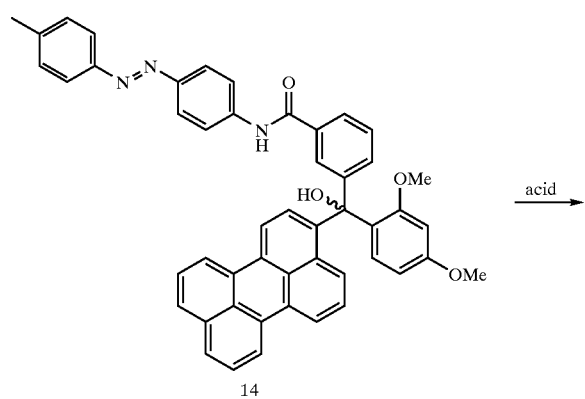

14

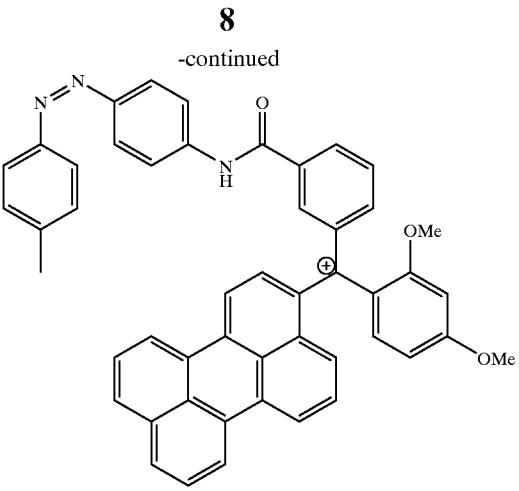

15

Conjugation of the azobenzene (or the stilbene) switch with a fluorophore playing the role of a photonic funnel will lead to the device being triggered by light of a different wavelength, again with a possibility of switching the components on and off by changing pH. The device can be used as a molecular switch, moving parts of the structure relative to each other.

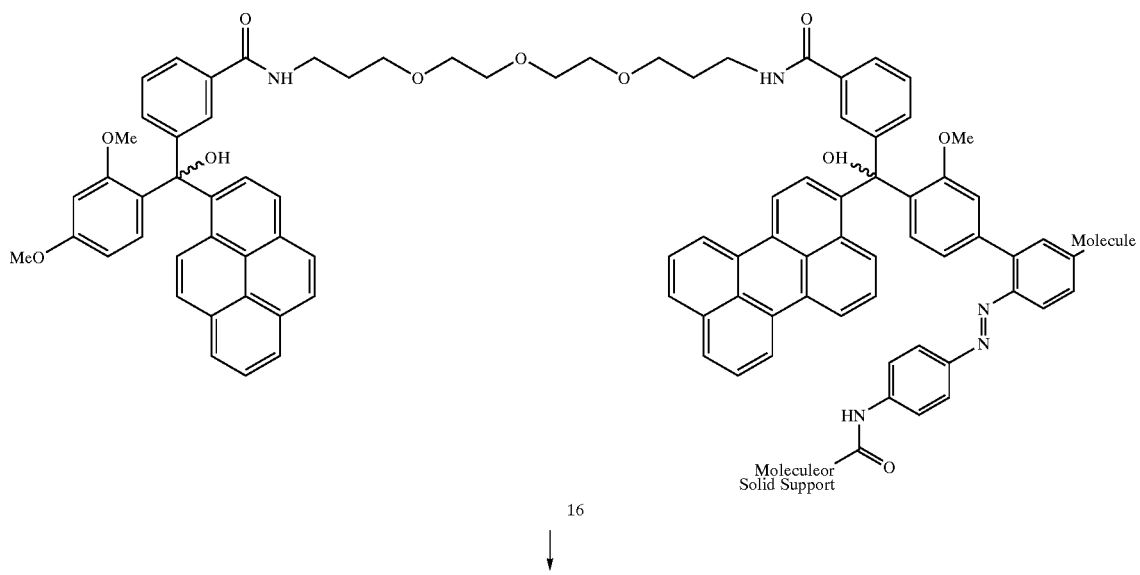

16

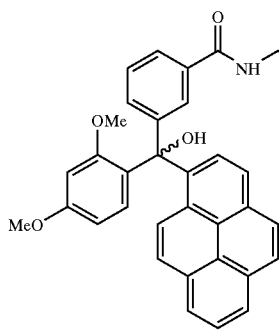
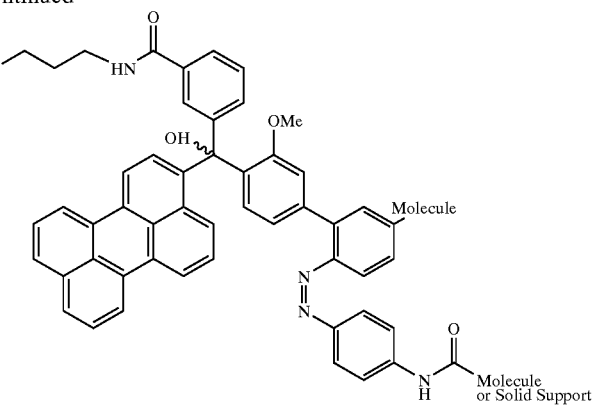

17

More complicated structures can be produced by utilizing the FRET-type transfer. Also, by polymerising such monomers into longer chains, it will be possible to create contractable polymers controlled by light and pH.

All the abovementioned properties of tags can be used both in solution and in solid-supported (surface-bound) applications.

Another potential application of these new tags can be in the field of electroluminiscent devices. For example, the fluorescent moieties bearing such fluorophores as perylene (blue colour dopant for PPV) or rubrene (yellow colour dopant) may be polymerised. Alternatively, they may be attached to a backbone such as a polyphenylenevinylene chain. This may lead to better and finer colour control as well as an improved hole transport (p-type of conductivity) through the polymer.

For solution-based assays, the fluorophores may be used to label (bio)molecules such as oligonucleotides. This will be simplified by using phosphoramidite reagents suitable for automated DNA synthesis, as shown for compounds 18 and 19.

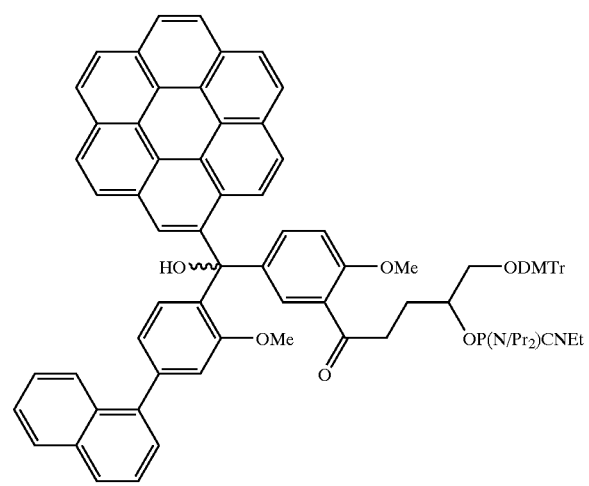

18

19

The reagents are readily synthesised, e.g. by acylation of aminopropane-2,3-diol with 4a–c, followed by dimethoxytritylation of the primary hydroxyl group and then by phosphitylation of the secondary hydroxyl group.

In addition to the use of pH, the triggering of trityl tags can also be achieved by using a (relatively) short wavelength laser. This leads to formation of cation radicals which also conjugates the aromatic moieties together. Tertiary amine- and sulphonium salt-based tags stay conjugated regardless of pH, but the properties of their fluorophore parts can be further controlled by pH.

The synthesis of PAH-containing trityl blocks can be simplified by conjugating a pre-synthesised universal trityl block with PAHs bearing appropriate functionalities. In that way, it is possible to substantially reduce the amount of synthetic steps. For instance, Heck coupling of pre-synthesised iodinated trityl block with alkinylated PAH yields trityl derivative of the corresponding PAH in just one step.

The following Examples illustrate the invention.

UV-spectra were measured on a Spectronic 2000 spectrophotometer, Milton Roy Co., USA. Fluorescence spectra were recorded on Perkin Elmer Luminescence Spectrometer LS 50 B. MALDI- and LDI-TOF mass-spectra were recorded on a PE-ABI Voyager™ Elite Reflectron Delayed Extraction Instrument. Spectra were acquired with an accelerating voltage of 25 KV and 100 ms delay in the positive ion mode. $^1$H-NMR spectra were recorded on a Varian Gemini 200 200 MHz spectrometer. HPLC was carried out on a Waters system (Milford, MA, USA). Chemicals were purchased from Aldrich Chemical Company (USA), Avocado Research Chemicals (UK), Lancaster Synthesis, Ltd (UK), and Acros Organics (Fisher Scientific, UK). Silica gel for column chromatography, UV254 TLC plates and solvents were from BDH/Merck.

In summary, a series of compounds has been made based on core trityl structure using PAHs as aryl substituents. Friedel-Crafts acylation of PAHs with 2,4-dimethoxybenzoyl chloride in the presence of AlCl$_3$ in DCM for pyrene or chlorobenzene for perylene and coronene gave 1-acylpyrene 2a, 3-acylperylene 2b and acylcoronene 2c (Scheme 1 shown below). These ketones were converted into corresponding R,S-oxazolyltritanols 3a–c using appropriate phenylmagnesium bromide as a nucleophile in Grignard synthesis. Further conversion yielded NHS-derivatives 4a (as pale yellow), 4b (as dark red) and 4c as yellow solids. NHS-esters 4a–c can be used for labelling of biomolecules or for derivatisation of surfaces. A labelling procedure may involve reacting 4a–c with an amino group(s)-containing analyte; corresponding model butylamides 7–9 were therefore synthesised, for fluorescence studies.

The compounds shown in the Schemes and their properties are:

1-(2,4-Dimethoxybenzoyl)pyrene (2a)

Pyrene (10,1 g; 0.05 mol) and 2,4-dimethoxybenzoyl chloride (10 g; 0.05 mol) were dissolved in 400 ml of anhydrous methylene chloride. Anhydrous aluminium chloride (6.6 g; 0.05 mol) was added to the reaction mixture in small portions over 1 h at 0° C. with intense stirring. The reaction mixture was stirred for another 2 h at 0° C., 2 h at rt and then poured onto a mixture of ice and HCl (500 ml) and transferred into a separating funnel. The organic layer was washed with water (1×500 ml), saturated NaHCO$_3$ (2×500 ml) and saturated NaCl (1×500 ml). The organic fraction was evaporated and recrystallised from toluene to give pyrenylketone as white solid (15.7 g; 86%). Found: C, 82.09; H, 4.81. $C_{25}H_{18}O_3$ (MW 366.41) requires C, 81.95; H, 4.95%. $^1$H-NMR (CDCl$_3$, d): 8.65–6.45 (m, 12 H, arom.), 3.91 (s, 3H, OCH$_3$), 3.55 (s, 3H, OCH$_3$). Mass-spectrum, MALDI-TOF: 388.89 (MI+Na; 15), 366.89 (100), 203.82 (40). Calculated exact mass for $C_{25}H_{18}O_3$:366.12559; found 366.12617 [1.6 ppm error].

3-(2,4-Dimethoxybenzoyl)perylene (2b)

The synthesis was carried out essentially as described for 2a, but chlorobenzene was used as a solven instead of methylene chloride. Yield: 53%. Found: C, 83.84; H, 4.69; $C_{29}H_{20}O_3$ (MW 416.47) requires C, 83.63; H, 4.84%. Mass-spectrum, MALDI-TOF: 416.92 (100), 252.65 (60). Calculated exact mass for $C_{29}H_{20}O_3$:416.14125; found 416.14125.

2,4-Dimethoxybenzoylcoronene (2c)

The synthesis was carried out essentially as described for 2a, but chlorobenzene was used as a solvent instead of methylene chloride. Yield after column chromatography (methylene chloride/ hexane): 48%. Found: C, 85.52; H, 4.21; $C_{33}H_{20}O_3$ (NM 464.51) requires C, 85.33; H, 4.34%. Mass-spectrum, MALDI-TOF: 464.22 (100), 300.1 (30). Calculated exact mass for $C_{33}H_{20}O_3$:464.14125; found 464.14189 [1.4 ppm error].

3-(4,4-Dimethyl-1,3-oxazoline-2-yl)phenyl Bromide m-Bromobenzoyl chloride (46 g, 0.21 mol) was dissolved in 250 ml of dry methylene chloride. To this ice-cooled solution, 46 g (0.51 mol, 2.5 eqv) of 2-amino-2-methylpropanol in 150 ml of dry methylene chloride was added dropwise for 2 h. The solution was stirred overnight at rt, and the precipitate was washed several times with methylene chloride. Combined fractions were evaporated, carefully dissolved in 350 ml of thionyl chloride and refluxed for 4 h. The reaction mixture was evaporated to ⅓, poured into 2 L of dry ether and kept overnight at 4° C. The precipitate of hydrochloride was dissolved in 1 L of water at 10° C., and 300 ml of 5 M KOH was added to it with stirring. The mixture was extracted with chloroform (3×350 ml), organic phase dried over CaCl$_2$ and evaporated. The resulting oil was silica gel-purified to give 46 g (86%) of colourless liquid. $^1$H-NMR (CDCl$_3$, d): 8.12 (s, 1H, 2-H, arom.), 7.88 (d, 1H, 6-H, arom.), 7.6 (d, 1H, 4-H, arom.), 7.28 (t, 1H, 5-H, arom.), 4.12 (s, 2H, CH$_2$), 1.48 (s, 6H, CH$_3$). Mass-spectrum, MALDI- TOF: 254.47 (MI, 100), 256.48 (MI, 100).

Compound 3a

Bromophenyl oxazoline (2.8 g, 0.011 mol) was dried by evaporation with dry toluene (2×20 ml) on rotary evaporator. It was then dissolved in 50 ml of dry THF and added to 0.27 g (0.012 mol) of magnesium turnings activated with iodine, MeI and RED-Al®. The mixture was refluxed for 3 h, cooled to rt and 2a (4 g, 0.0105 mol) in 10 ml of dry THF was added dropwise. The mixture was gently refluxed for 6 h, cooled to rt and 3 ml of water was added with stirring. Organic phase was carefully decanted and residue washed several times with small portions of THF. Combined organic fractions were evaporated and purified (flash chromatography) to give 4.31 g (73%) of light yellow solid. Found: C, 79.66; H, 5.94; N, 2.71. $C_{36}H_{31}NO_4$ (MW 541.64) requires C, 79.83; H, 5.77; N, 2.59%. $^1$H-NMR (CDCl$_3$, d): 8.75–6.38 (m, 16H, arom.), 3.95 (s, 2H, CH$_2$), 3.81 (s, 3H, OCH$_3$), 3.7 (s, 3H, OCH$_3$), 1.36 (s, 6H, CH$_3$). Mass-spectrum, MALDI-TOF: 541.48 (100), 524.41 (5). Calculated exact mass for $C_{36}H_{31}NO_4$:541.22531; found:541.22740 [3.8 ppm error].

Compound 3b

Perylenyl-containing oxazolyl tritanol was synthesized as in a way similar to that described for 3a, with 15 h reflux time upon addition of the ketone. Yield: 64%. Found: C, 81.41; H, 5.50; N, 2.33. $C_{40}H_{33}NO_4$ (MW 591.69) requires C, 81.20; H,.5.62; N, 2.37%. $^1$H-NMR (CDCl$_3$, d): 8.4–6.25 (m, 18H, arom.), 4.12 (s, 2H, CH$_2$), 3.83 (s, 3H, OCH$_3$), 3.75 (s, 3H, OCH$_3$), 1.39 (s, 6H, CH$_3$). Mass-spectrum, MALDI-TOF: 591.47 (100), 453.33 (70). Calculated exact mass for $C_{40}H_{33}NO_4$:591.24096; found 591.24131 [0.6 ppm error].

Compound 3c

Coronenyl-containing oxazolyl tritanol was synthesized as in a way similar to that described for 3a, with 15 h reflux time upon addition of the ketone. Yield: 49%. Found: C, 82.58; H, 5.19; N, 2.21. $C_{44}H_{33}NO_4$ (MW 639.74) requires C, 82.61; H, 5.20; N, 2.19%. $^1$H-NMR (CDCl$_3$, d): 8.95–6.25 (m, 18H, arom.), 4.05 (s, 2H, CH$_2$), 3.8 (d, 6H, OCH$_3$), 1.4 (s, 6H, CH$_3$). Mass-spectrum, MALDI-TOF: 639.17 (90), 621.15 (100), 486.88 (20), 463.97 (10), 339.9

(40), 302.13 (5). Calculated exact mass for $C_{44}H_{33}NO_4$: 639.24096; found 639.24003 [1.5 ppm error].

Compound 4a

The solution of 3a (5.6 g, 0.01 mol) in 100 ml of 80% acetic acid was kept at 72° C. for 48 h, evaporated and then evaporated with water (2×50 ml). The product was dissolved in 75 ml of 50% EtOH in water, refluxed for 3 h and evaporated to ⅓. The mixture was then dissolved in 100 ml of water and acidified with 3M HCl to pH 1–2. The precipitate was dissolved in chloroform, dried ($Na_2SO_4$) and evaporated to dryness and additionally dried in vacuo overnight. Carboxylic acid obtained was dissolved in 100 ml of dry THF. N-hydroxysuccinimide (1.15 g, 0.01 mol) was added and the mixture was cooled to 0° C. Dicyclohexylcarbodiimide (2.1 g, 0.012 mol) in 10 ml of dry THF was added dropwise with stirring. The reaction mixture was stirred 1 h at 0° C. and overnight at rt. Dicyclohexylurea was filtered off and organic phase was evaporated to dryness and purified (flash chromatography) to give 4 g (66%) of yellow-white solid. $R_f$ (2% MeOH in $CDCl_3$): 0.38. Found: C, 74.0; H, 4.52; N, 2.33. $C_{36}H_{27}NO_7$ (MW 585.60) requires C, 73.84; H, 4.65; N, 2.39%. $^1$H-NMR ($CDCl_3$, d): 8.75–6.24 (m, 16H, arom.), 3.83 (s, 3H, $OCH_3$), 3.75 (s, 3H, $OCH_3$), 2.87 (s, 4H, $CH_2$). Mass-spectrum, MALDI-TOF: 585.3 (15), 568.3 (10), 488.4 (60), 444.4 (100). Calculated exact mass for $C_{36}H_{27}NO_7$: 585.17875; found 585.17993 [2 ppm error].

Compound 4b

Perylenyl-based NHS-tritanol was synthesized in a way similar to that described for 4a. Yield: 61%. $R_f$ (2% MeOH in $CDCl_3$): 0.55. Found: C, 75.66; H, 4.59; N, 2.13. $C_{40}H_{29}NO_7$ (MW 635.66) requires C, 75.58; H, 4.60; N, 2.20%. $^1$H-NMR ($CDCl_3$, d): 8.38-6.26 (m, 18H, arom.), 3.77 (d, 6H, $OCH_3$), 2.89 (s, 4H, $CH_2$). Mass-spectrum, MALDI-TOF: 634.99 (8), 618.2 (20), 538.3 (6), 497.2 (100), 400.2 (35). Calculated exact mass for $C_{40}H_{29}NO_7$:635.19440; found 635.19651 [3.3 ppm error].

Compound 4c

Coronenyl-based NHS-tritanol was synthesized in a way similar to that described for 4a, but trifluoroacetic acid was used instead of acetic acid, and the reaction mixture was kept at rt for 72 h. Yield: 58%. $R_f$ (2% MeOH in $CDCl_3$): 0.45. Found: C, 77.15; H, 4.19; N, 2.16. $C_{44}H_{29}NO_7$ (MW 683.7) requires C, 77.30; H, 4.28; N, 2.05%. $^1$H-NMR ($CDCl_3$, d): 8.98–6.55 (m, 18H, arom.), 3.85 (d, 6H, $OCH_3$), 2.94 (s, 4H, $CH_2$). Mass-spectrum, MALDI-TOF: 683.34 (20), 666.53 (100), 547.47 (40), 466.72 (35). Calculated exact mass for $C_{44}H_{29}NO_7$:683.19440; found 683.19673 [3.4 ppm error].

Butylamides (7–9)

Corresponding butylamides were synthesized by adding 0.1 M solutions of butylamine in THF to equivalent amounts of 0.1 M solutions of 4a–c in THF and keeping them at rt for 1 h. The reaction mixtures were diluted with ethyl acetate, washed with sat. $NaHCO_3$, sat. NaCl, evaporated and used without further purification. For spectral data on these compounds, see FIGS. 1–4.

7. Calculated exact mass for $C_{36}H_{33}NO_4$:543.24096; found 543.24333 [4.3 ppm error].
8. Calculated exact mass for $C_{36}H_{33}NO_4$:593.25661; found 593.25660
9. Calculated exact mass for $C_{44}H_{35}NO_4$:641.25661; found 641.25707 [0.7 ppm error].

Bis-tritylated Compound 10

The title compound was synthesized by stepwise acylation of excess of 4,7,10-trioxa-1,13-tridecanediamine with 4b in methylene chloride, followed by washing with sat. $NaHCO_3$ to remove non-reacted diamine. Mono-acylated compound was then further acylated in methylene chloride with one equivalent of 4a. Mass-spectrum, MALDI-TOF: 1232.95 (MI+$Na^+$ (10)), 1210.54 (10), 1193.04 (100), 1175.28 (40). Calculated exact mass for $C_{78}H_{70}N_2O_{11}$:1210.49796; found 1210.49938 [1.2 ppm error].

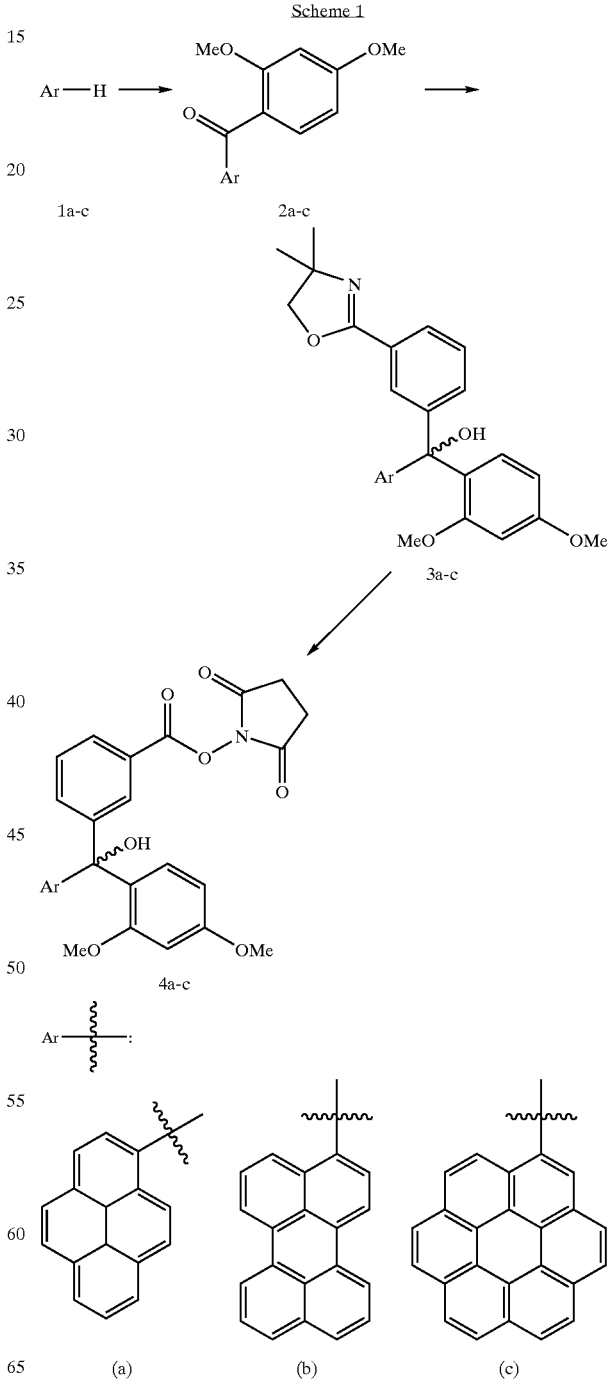

Scheme 2

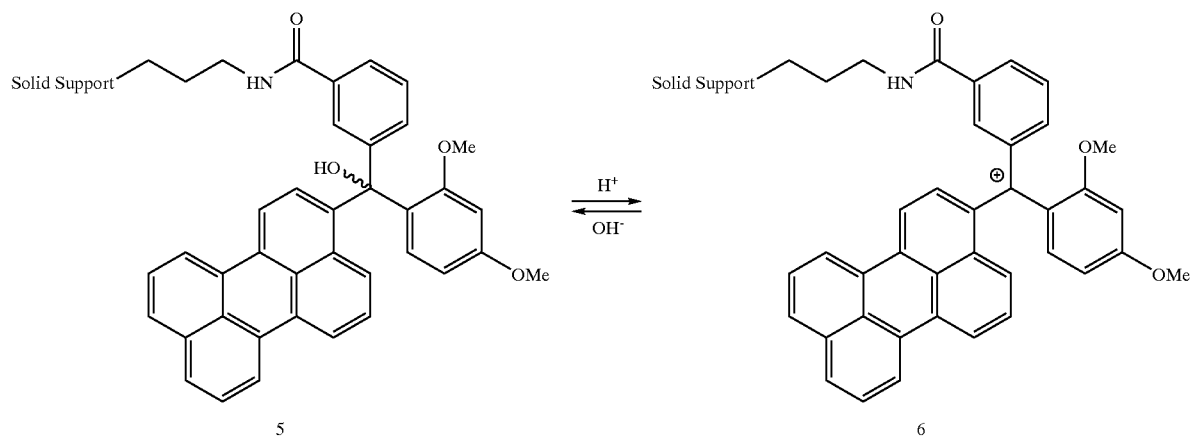

References

1. Smith, et al., *J. Am. Chem. Soc.,* 1961, 84, 430–440.
2. Fisher et al., *Nucleic Acids Res.,* 1983, 11, 1589–1599.
3. Fourrey et al., *Tetrahedron Lett.,* 1987, 28, 5157–5160.
4. Gildea et al., *Tetrahedron Lett.,* 1990, 31, 7095–7098.
5. Leikauf et al., *Tetrahedron,* 1995, 51, 3793–3802.
6. Patel et al., *Bioorg. Med. Chem. Lett.,* 1995, 5, 507–512.
7. Letsinger et al., *J. Am. Chem. Soc.,* 1975, 97, 7197–7198.
8. Matteucci et al., *Tetrahedron Lett.,* 1980, 21, 3243–3246.
9. Herz, *J. Am. Chem. Soc.,* 1975, 97, 6777–6785.
10. Shchepinov et al., *Nucl. Acids Symp. Ser.,* 1999, 42, 107–108.
11. Wei et al., Siuzdak, G. *Nature,* 1999, 399, 243–246.
12. Smith et al., *Nature,* 1986, 321, 674–679.
13. Cardullo et al., *Proc. Natl. Acad Sci. USA,* 1988, 85, 8790–8794.
14. Tyagi etal., *Nature Biotech.,* 1996, 14, 303–308.
15. Lewis et al., *J. Am. Chem. Soc.,* 1997, 119, 5451–5452.
16. Mao et al., *Nature,* 1999, 397, 144–146.
17. Dobrikov et al., *NucleosidesNucleotides,* 1999, 18, 1517–1518.
18. Reines et al., *Nucleic Acids Res.,* 1974, 1, 767–78-6.
19. Schena et al., *Science,* 1995, 270, 467–470.

What is claimed is:

1. A compound having the formula 11, 12 or 13

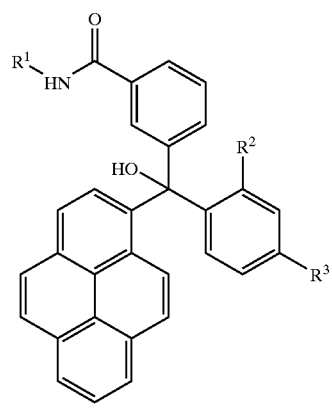

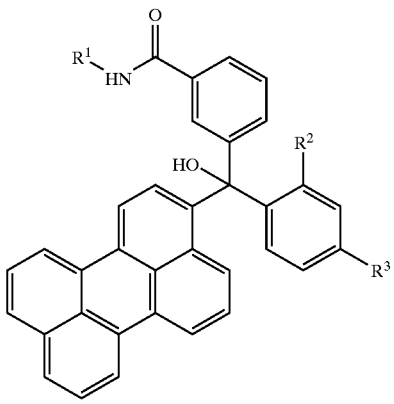

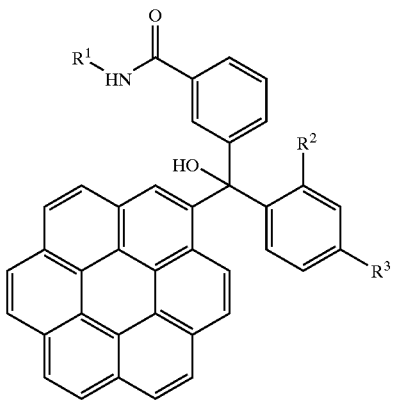

wherein $R^1$ is an $C_1$–$C_{20}$, alkyl group and $R^2$ and $R^3$ are either H or McO—, and wherein said compound is linked to a biomolecule solid phase.

2. The compound according to claim 1, wherein $R^1$ is $C_4$ alkyl.

3. A fluorescence-resonant compound comprising two different compounds, the compounds having the formula 11, 12, or 13

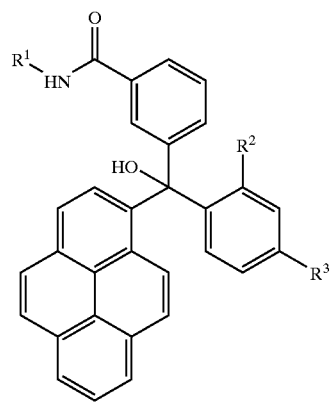
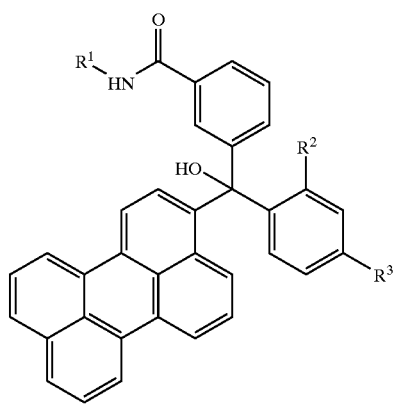
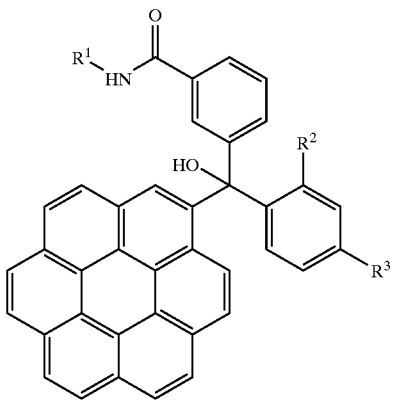
wherein $R^1$ is an $C_1$–$C_{20}$ alkyl group and $R^2$ and $R^3$ are either H or McO—, and wherein the two different compounds are linked together via the respective $R^1$ groups.
4. The compound according to claim 3, wherein $R^1$ is $C_4$ alkyl.
5. The compound according to claim 1, wherein said biomolecule is a nucleic acid, amino acid, or peptide.
* * * * *

UNITED STATES PATENT AND TRADEMARK OFFICE
CERTIFICATE OF CORRECTION

PATENT NO. : 6,809,220 B2
DATED : October 26, 2004
INVENTOR(S) : Mikhail Sergeevich Shchepinov and Edwin Mellor Southern It is certified that error appears in the above-identified patent and that said Letters Patent is hereby corrected as shown below:

Column 16,
Line 59, "McO—" should read -- MeO— --.

Column 18,
Line 22, "McO—" should read -- MeO— --.

Signed and Sealed this

Nineteenth Day of April, 2005

JON W. DUDAS
*Director of the United States Patent and Trademark Office*